(12) United States Patent
Giori

(10) Patent No.: US 7,179,245 B2
(45) Date of Patent: Feb. 20, 2007

(54) FLUSHABLE BODY WASTE COLLECTION POUCH, POUCH-IN-POUCH APPLIANCE USING THE SAME, AND METHOD RELATING THERETO

(75) Inventor: Claudio Giori, Riverwoods, IL (US)

(73) Assignee: Hollister Incorporated, Libertyville, IL (US)

( * ) Notice: Subject to any disclaimer, the term of this patent is extended or adjusted under 35 U.S.C. 154(b) by 135 days.

(21) Appl. No.: 10/969,524

(22) Filed: Oct. 20, 2004

(65) Prior Publication Data

US 2005/0084634 A1 Apr. 21, 2005

Related U.S. Application Data

(60) Provisional application No. 60/512,759, filed on Oct. 21, 2003.

(30) Foreign Application Priority Data

Oct. 21, 2003 (DK) ................. 2003 01550

(51) Int. Cl.
*A61F 5/445* (2006.01)
(52) U.S. Cl. .............. 604/332; 604/327; 428/35.2
(58) Field of Classification Search .......... 604/327, 604/332, 333, 335, 334, 336, 337, 338, 339, 604/340, 341, 342, 343–345; 428/35.2
See application file for complete search history.

(56) References Cited

U.S. PATENT DOCUMENTS

| | | | |
|---|---|---|---|
| 3,934,587 A | | 1/1976 | Gordon |
| 4,213,458 A | | 7/1980 | Nolan et al. |
| 4,372,311 A | * | 2/1983 | Potts .......................... 604/364 |
| 4,518,087 A | * | 5/1985 | Goglio ........................ 383/210 |
| 4,687,711 A | * | 8/1987 | Vietto et al. ................ 428/515 |
| 4,762,738 A | * | 8/1988 | Keyes et al. ................ 428/34.3 |
| 4,816,027 A | * | 3/1989 | Gilchrist et al. ............ 604/339 |
| 4,826,493 A | * | 5/1989 | Martini et al. .............. 604/327 |
| 4,906,495 A | * | 3/1990 | Martini et al. ............. 428/36.7 |
| 4,946,720 A | * | 8/1990 | Oishi et al. ................ 428/35.4 |
| 5,009,648 A | * | 4/1991 | Aronoff et al. ............. 604/332 |
| 5,104,390 A | | 4/1992 | Yum et al. |
| 5,108,807 A | | 4/1992 | Tucker |

(Continued)

FOREIGN PATENT DOCUMENTS

EP 1022127 A2 7/2000

OTHER PUBLICATIONS

Copy of Danish Office Action, dated Mar. 18, 2004, translation, and Denmark application PA 2003 01550, filed Oct. 21, 2003.

(Continued)

*Primary Examiner*—Tatyana Zalukaeva
*Assistant Examiner*—Paula L. Craig
(74) *Attorney, Agent, or Firm*—Marshall, Gerstein & Borun LLP

(57) ABSTRACT

A biodegradable and toilet-flushable body waste collection pouch, and an appliance in which such pouch constitutes the inner pouch of a peelably separable pouch-in-pouch system, are disclosed. The walls of the inner pouch are composed of an ultra-thin, heat-sealable film impermeable to body wastes comprising a plasticized biodegradable polyester or copolyester externally covered by a soft, porous, water-disintegratable cover layer of biodegradable and water-dispersible fibers.

40 Claims, 1 Drawing Sheet

U.S. PATENT DOCUMENTS

| | | | | |
|---|---|---|---|---|
| 5,110,390 | A * | 5/1992 | Martini et al. | 156/244.11 |
| 5,227,415 | A | 7/1993 | Masuda et al. | |
| 5,254,607 | A | 10/1993 | McBride et al. | |
| 5,391,423 | A | 2/1995 | Wnuk et al. | |
| 5,407,979 | A | 4/1995 | Wu et al. | |
| 5,417,677 | A | 5/1995 | Schneider et al. | |
| 5,422,387 | A | 6/1995 | Toms et al. | |
| 5,423,782 | A * | 6/1995 | Wolrich | 604/339 |
| 5,446,079 | A * | 8/1995 | Buchanan et al. | 524/41 |
| 5,468,526 | A | 11/1995 | Allen et al. | |
| 5,470,526 | A * | 11/1995 | Wilfong et al. | 428/36.6 |
| 5,540,962 | A | 7/1996 | Suskind | |
| 5,591,144 | A * | 1/1997 | Smith et al. | 604/327 |
| 5,674,578 | A * | 10/1997 | Giori | 428/35.4 |
| 5,679,421 | A | 10/1997 | Brinton, Jr. | |
| 5,690,622 | A | 11/1997 | Smith et al. | |
| 5,753,782 | A * | 5/1998 | Hammond et al. | 525/450 |
| 5,776,120 | A * | 7/1998 | Shelley et al. | 604/339 |
| 5,785,695 | A * | 7/1998 | Sato et al. | 604/339 |
| 5,786,408 | A | 7/1998 | Kuroda et al. | |
| 5,821,286 | A | 10/1998 | Xu et al. | |
| 5,865,819 | A | 2/1999 | Cisko, Jr. et al. | |
| 5,889,140 | A * | 3/1999 | Watanabe | 528/354 |
| 5,912,059 | A * | 6/1999 | Jones et al. | 428/35.2 |
| 5,938,647 | A | 8/1999 | Smith | |
| 5,939,467 | A | 8/1999 | Wnuk et al. | |
| 5,969,089 | A | 10/1999 | Narayan et al. | |
| 6,033,758 | A * | 3/2000 | Kocher et al. | 428/138 |
| 6,075,118 | A | 6/2000 | Wang et al. | |
| 6,127,512 | A | 10/2000 | Asrar et al. | |
| 6,156,929 | A | 12/2000 | Chandler et al. | |
| 6,248,380 | B1 * | 6/2001 | Kocher et al. | 426/127 |
| 6,248,442 | B1 * | 6/2001 | Kong et al. | 428/355 EN |
| 6,514,602 | B1 | 2/2003 | Zhao et al. | |
| 6,552,162 | B1 * | 4/2003 | Wang et al. | 528/354 |
| 7,045,183 | B2 * | 5/2006 | Amano et al. | 428/35.2 |
| 2002/0064614 | A1 | 5/2002 | Turnbull | |
| 2002/0197425 | A1 * | 12/2002 | Wolf et al. | 428/35.2 |
| 2004/0059306 | A1 * | 3/2004 | Tsal et al. | 604/332 |

OTHER PUBLICATIONS

Annex to Form PCT/ISA/206 (Communication Relating to the Results of the Partial International Search for PCT/US2004/034760).

* cited by examiner

FLUSHABLE BODY WASTE COLLECTION POUCH, POUCH-IN-POUCH APPLIANCE USING THE SAME, AND METHOD RELATING THERETO

RELATED APPLICATIONS

This application claims priority from U.S. Provisional Patent Application Ser. No. 60/512,759 filed Oct. 21, 2003 and Danish Patent Application Serial No. 2003/01550, filed Oct. 21, 2003.

BACKGROUND AND SUMMARY

This invention relates to flushable body waste collection pouches, and particularly to a biodegradable pouch suitable for use as the toilet-disposable inner pouch of a pouch-within-a-pouch ostomy appliance of the type generally disclosed in U.S. Pat. No. 5,865,819 and in copending U.S. Pat. Appl 10/969,523 claiming priority from provisional application 60/512,760 filed Oct. 21, 2003 and bearing the name of Claudio Giori as a co-inventor. The disposable pouch has a pair of walls secured together along their peripheral edges to define a waste-receiving chamber, and one of the side walls has a body waste receiving opening which communicates with that chamber. External attachment means are provided about the opening for attachment of the pouch (or pouch assembly) to a wearer.

The only inner pouch currently on the market is a pouch available from Welland Medical covered by U.S. Pat. No. 5,938,647. This pouch is made of hot water soluble polyvinylalcohol. The problem with polyvinylalcohol is that it becomes brittle and noisy upon aging and has limited biodegradability. Thus, there is a need for an inner pouch file that is flexible, water impermeable, has low noise (an important requirement for ostomy and fecal incontinence pouches) and good biodegradability.

The walls of a pouch embodying this invention are composed of a thin, heat sealable (including RF sealable) and liquid-impermeable monolayer film of a composition comprising a plasticized biodegradable aliphatic polyester, or a plasticized biodegradable aliphatic-aromatic copolyester, or blends thereof, covered by a water-disintegratable layer of biodegradable and water-dispersible fibers, most preferably cellulosic fibers, bonded thereto. The polyester or copolyester is blended with an aliphatic ester plasticizer such as triethylcitrate or vegetable oil. Such a plasticizer imparts greater flexibility to the film, reduces film noise upon wrinkling, and allows extrusion of the resin into films or coatings as thin as 10 microns (0.8 mil) or less. It has also been found that the presence of the plasticizer effectively increases the rate of biodegradation of the film. Starch may also be used advantageously as a biodegradable plasticizer.

The composition of the film may comprise a blend of about 70% to 95% by weight of the biodegradable aliphatic polyester or aliphatic-aromatic copolyester and 5% to 30% of a biodegradable plasticizer or plasticizers. More desireably, the blend is within the range of about 75% to 93% polyester or copolyester and about 7% to 25% plasticizer(s). A preferred composition is believed to be about 90% polyester or copolyester and about 10% plasticizer(s).

The aliphatic polyester may comprise a polymer made by ring-opening polymerization of a lactone, preferably polycaprolactone. The aliphatic-aromatic copolymer may comprise a condensation product of a glycol with a combination of an aliphatic diacid and aromatic diacid, wherein the aromatic diacid is less than 20% by mole.

To enhance biodegrability, minimize noise, and reduce cost, the film should be ultra-thin, having a thickness no greater than about 40 microns (1.57 mil). A preferred thickness range is believed to be about 6 to 40 microns (0.24 to 1.57 mil) with a more preferred range being about 10 to 35 microns (0.39 to 1.38 mil). Particularly effective results are believed to occur when the thickness range is about 15 to 30 microns (0.59 to 1.18 mil).

The ultra-thin monolayer film, having the advantages and features described above, is reinforced by the water-disintegratable cover layer defining the outer surfaces of the pouch. The cover layer is composed of a random arrangement of water-dispersible fibers, has no non-water-soluble binder (and preferably no binder at all) and has significant dry strength with virtually no elongation but lacks wet strength. Tissue paper having a high cellulosic fiber content, preferably 100%, is believed particularly effective. The monolayer film may be secured uninterruptedly throughout one of its side surfaces to the tissue or other reinforcing substrate by any suitable means. While adhesive attachment (as by a water-soluble and biodegradable adhesive) is considered feasible, it is believed more effective to extrude the polyester or copolyester onto the paper substrate to form a thin but uninterrupted coating thereon or to laminate the two layers together with heat, with the attachment between the opposing surfaces of the two layers in either case being produced with heat and being mechanical in nature. As long as the external surface of the pouch is in a dry state, the tissue paper covering offers mechanical strength, softness, and noise reduction but, upon exposure to water, as when the pouch is discarded into a flush toilet, the tissue disintegrates rapidly and is believed to contribute to flushability by rapidly absorbing water, wetting the film surface, and reducing pouch buoyancy.

An important aspect of this invention lies in the strength, or lack of strength, of the attachment between substantially one entire surface of the cover layer (excluding its peripheral edge portions) and the film that together form each wall of the flushable pouch. (It is along such peripheral edge portions that the layers are securely heat-sealed together to form a completed pouch.) To avoid the formation of unacceptable pinholes in the film, it is essential that none of the fibers of the cover layer extends through the film or even penetrates the film to any appreciable extent. Since the film may be any of a number of different thicknesses, but is ultra-thin in any event, measuring the maximum extent of penetration, if any, is not considered feasible. However, it has been found that no appreciable penetration is achieved, and no pinholes are formed, if the extent of bonding between the paper and film layers is such that the two layers may be peeled away from each other (when dry), with both layers remaining intact, by the application of 180-degree peel forces in the range of about 2 to 10 g/in (0.02 to 0.1 Newtons/in), preferably about 3 to 6 g/in (0.03 to 0.06 Newtons/in). Under such conditions, the layers are found to be bonded together with sufficient strength to maintain the integrity of the pouch wall during use but without risk of unacceptable fiber penetration.

Since the polyester or copolyester films are heat sealable (including RF sealable), the films may be readily converted into pouches using conventional heat sealing methods. Although the film is covered by a soft, flexible and fibrous backing layer as described above, heat sealing is nevertheless readily achieved because the polymeric layers of the pouch walls face inwardly and may therefore be securely welded to each other. Where the pouch serves as the inner pouch of a two-pouch system, it has been found that where the inner pouch has a fibrous and porous cover layer of tissue paper or other suitable fibrous and porous substrate, heat sealing between the film of the inner pouch, the fibrous and porous cover layer, and the film of the outer pouch, as along the peripheral edges of the two pouches, may nevertheless occur. In such a case, the seal between the walls of the outer pouch and the fibrous layer of the inner pouch walls is weaker than the seal between the two walls of the inner pouch, thereby allowing the outer pouch to be torn or peeled away from the inner pouch without adversely affecting the integrity of the inner pouch, at which time the still-intact inner pouch and its contents may be discarded into the water of a toilet bowl to commence the disintegration and biodegradation process.

In such a pouch-in-pouch appliance, where the walls of the flushable inner pouch are composed of thermoplastic film and tissue paper layers weakly bonded together, it is essential that peeling away of the outer pouch not cause delamination of the paper and film layers of the inner pouch since, as already noted, the paper layer is believed to contribute significantly to the flushability of the inner pouch. Also, retention of the soft paper layer by the inner pouch provides tactile benefits for the user who must handle and remove the inner pouch for toilet disposal, as well as assuring the user that the step of peeling away of the outer pouch walls has not compromised the integrity of the inner pouch. An important aspect of this invention therefore lies in avoiding the risks of such delamination by selecting a thermoplastic material for the outer pouch that has a melting temperature greater than that of the thermoplastic material of the inner pouch. Since the fibers of the non-thermoplastic cover layer penetrate the thermoplastic films of both pouches in the zone of the peripheral heat seal, and since the thermoplastic material of the inner pouch has a lower melting temperature, the fiber penetration into the film of the inner pouch along the peripheral heat seal is greater than into the film of the outer pouch and insures that the paper layer will preferentially remain with the inner pouch as the walls of the outer pouch are peeled away.

The peripheral heat seal therefore simultaneously joins the multiple layers together in different ways to achieve peelability of the outer pouch walls away from the fibrous cover layer of the inner pouch, the retention of the fibrous cover layer by the inner pouch, and the true heat-sealing or welding together of the walls of the inner pouch along their peripheral edges.

Other features and advantages of the invention will become apparent as the specification proceeds.

DETAILED DESCRIPTION OF PREFERRED EMBODIMENTS

The polyester or copolyester film material of an ostomy pouch or fecal incontinence pouch embodying this invention is obtained by chemical synthesis rather than by a fermentation process. Polyester or copolyester films produced by a fermentation process are considered unsuitable because they tend to be brittle and cannot be converted into thin flexible films. Examples of synthetic biodegradable polyesters are aliphatic polyesters such as polycaprolactone ("Tone" from Dow Chemical) and aliphatic-aromatic copolyesters with less than 20% by mole of aromatic diacid component ("Estar Bio" from Eastman Chemical, "Ecoflex" from BASF). A synthetic biodegradable polyester precompounded with biodegradable plasticizers and suitable for thin film extrusion is available commercially from Petroplast Vinora under the designation "KF02B".

Figure 1:
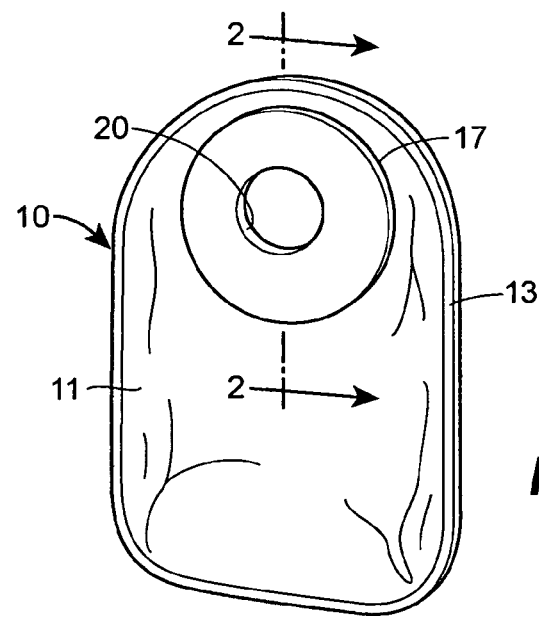
FIG. 1 is an elevational view of a flushable body waste collection pouch embodying the invention.
Figure 2:
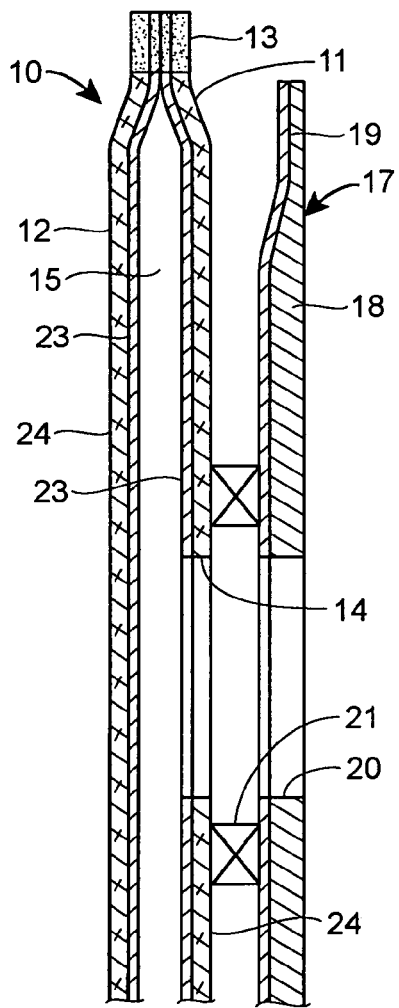
FIG. 2 is a somewhat-schematic vertical sectional view taken along line 2—2 of FIG. 1.

Referring to FIGS. 1 and 2 of the drawings, the numeral 10 generally designates a toilet-flushable body waste collection pouch with proximal (rear or bodyside) and distal (front) walls 11 and 12 having their peripheral edges joined together along a heat seal zone 13. For purposes of illustration, an ostomy pouch is shown, but the invention is applicable to other body waste collection pouches such as fecal incontinence pouches. Also, the terms "heat seal" and "heat sealing" should here be understood to include other forms of thermoplastic welding such as RF sealing. As shown, the proximal or bodyside wall is provided with an opening 14 communicating with the chamber 15 of the pouch.

The appliance 10 includes a faceplate 17 having a soft, pliant adhesive layer 18 for adhesive attachment to the peristomal skin surfaces of a wearer. A cover film 19 extends over the pouch-facing surfaces of the faceplate's adhesive layer 18, and a stoma-receiving opening 20 is provided in the faceplate in alignment with the opening 14 in the pouch. Attachment means 21 is schematically illustrated in FIG. 2 for joining the faceplate and pouch together. Such attachment means may take the form of a releasable mechanical coupling or a separable adhesive seal, all as well known in the art. For purposes of this embodiment of the invention, which focuses on pouch 10 and the materials from which it is formed (and the combination of that pouch with an outer pouch 10'), the attachment 21 is critical only to the extent that there must be some means around the stoma-receiving opening 14 for securing the pouch to a wearer.

Pouch 10 has its walls 11 and 12 formed of an ultra-thin heat-sealable (including RF sealable) liquid and gas impermeable film 23 externally bonded to a thin water-disintegratable cover layer 24. As previously stated, the film 23 is of a composition comprising a biodegradable, thermoplastic and heat-sealable, aliphatic polyester, or aliphatic-aromatic copolyester, or blends thereof, combined with a biodegradable plasticizer or combination of such plasticizers. The soft, flexible, water disintegratable cover layer 24 is composed of a random arrangement of water-dispersible non-thermoplastic fibers, preferably cellulosic fibers, and has significant tensile strength when dry but lacks such strength when wet, all as already described. The two layers are mechanically bonded together, preferably by heat, in such a way that despite the ultra-thin character of the film and the fibrous nature of the cover layer, there is no significant penetration of the fibers into the film and no formation of pinholes through the film. While some very limited penetration of the fibers into the film may exist to produce the weak mechanical bond between the layers, the penetration is so slight and the bonding forces so weak that the two layers (when dry) may be easily peeled apart with each layer remaining intact during and following such a peeling operation. More specifically, the mechanical attachment between the film and cover layer must be sufficiently weak to allow separation by the application of a 180 degree peeling force of about 2 to 10 g/in (0.02 to 0.1 Newtons/in), preferably about 3 to 6 g/in (0.03 to 0.06 Newtons/in), when tested in accordance with TAPPI Test Method UM502 (1991), all with little or no evidence of fiber retention by the film. Under such circumstances, the separated film will be free of pinholes that might otherwise cause fluid (liquid) leakage of the laminated two-layer product in use.

Figure 3:
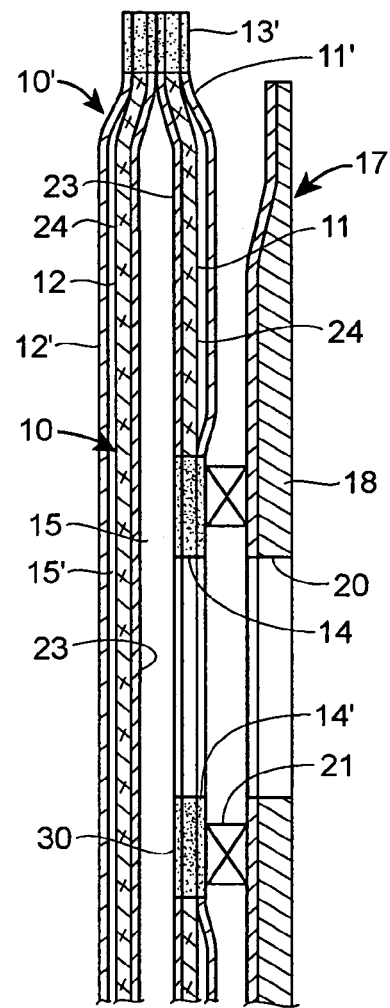
FIG. 3 is a sectional view similar to FIG. 2 but showing the flushable pouch as the inner pouch of a pouch-in-pouch appliance.

The water-disintegratable cover layer of non-thermoplastic water-dispersible fibers also plays an important role when the pouch serves as the inner pouch of a two-pouch (pouch-in-pouch) appliance as shown in FIG. 3. As there shown, pouch 10 is disposed within the chamber 15' of an outer pouch 10'. The peripheral edge portions of the two pouches may be joined together by heat sealing 13' which should be understood here to include RF sealing. The outer pouch 10' is of conventional construction and composed of any of a variety of known thermoplastic film materials that have a sufficiently high heat sealing or melting temperature and that are impermeable to liquids, gases and odors. It includes a proximal (rear or bodyside) wall 11' and a distal (front) wall 12' with the proximal wall having a stoma-receiving opening 14' aligned with the corresponding opening 14 of the inner pouch. The two pouches are sealed together, as by heat seal 30, about their respective openings. Therefore, body waste passing into the appliance can only enter the inner pouch and not the space between the two pouches.

As brought out in the aforementioned copending application, the disclosure of which is incorporated by reference herein, the peripheral seal 13' and the seal 30 about stoma openings 14, 14' are peelable seals that allow the proximal and distal walls 11' and 12' of the outer pouch to be peeled away from the inner pouch without disrupting the integrity of the peripheral seal that holds the walls of the inner pouch together. Thus, the walls of the outer pouch may be peeled away to expose the biodegradable inner pouch 10 so that the latter may be discarded along with its contents into a flush toilet. The outer pouch 10', which may or may not be biodegradable, may then be placed into any suitable waste receptacle.

As already noted, the fibrous and porous water-disintegratable layer 24 and the film layer 23 that together form the walls of the inner pouch have their major surfaces areas only weakly bonded together, allowing them to be separated intact from each other with the application of only limited peeling force. However, that does not include the peripheral heat seal zone 13' of the pouch shown in FIG. 3, where the film layers 23 of the inner pouch are securely heat sealed or welded to each other and also penetrate the pores of the peripheral zones of the fibrous layers 24 to produce a secure bond with the fibrous layers along the periphery of the inner pouch. The peripheral zones of the fibrous layers are also penetrated to at least some extent by the heat sealable material forming the walls 11' and 12' of the outer pouch 10'. However, the strength of the bond in the peripheral zones between the fibrous layers and the films of the inner pouch is much greater than between the fibrous layers and the thermoplastic films forming the walls of the outer pouch because the melting temperature of the inner pouch film material is substantially lower than the melting temperature of the outer pouch film material. The result is that when a user peels away the walls of the outer pouch to expose the inner pouch, the water-disintegratable, non-heat-sealable tissue paper layers of the inner pouch remain as part of the inner pouch and are not stripped away with the walls of the outer pouch.

Differential scanning calorimetry (DSC) can be used to measure the melting point of candidate film materials and to predict if a certain combination of films might be suitable for the inner and outer pouches. For example, it has been found that a biodegradable plasticized polyester available from Petroplast Vinora under the designation KF02B has a DSC melting peak of 65 degrees C. A known multilayer barrier film currently used commercially for ostomy pouches has a heat-sealable skin layer of poly(ethylene vinylacetate) (EVA) with a DSC melting peak of 88 degrees C. Because of this difference in melting temperatures, it is possible to control heat sealing conditions so that the tissue layer in the peripheral areas of the pouch walls exhibits a stronger bond with the inner pouch film than with the outer pouch film following a heat sealing operation (including RF sealing). As a result, the outer pouch can be peeled away without causing separation of the tissue layer from the inner pouch film. A melting temperature differential of at least 10 degrees C. is believed to be needed to control layer separation.

To facilitate the step of manually peeling away the proximal and distal walls of outer pouch 10', such walls may be provided with gripping tabs (not shown) that project outwardly beyond the peripheral edges of inner pouch 10.

The walls of the inner pouch must be impermeable to fluid and solid body wastes, and the biodegradable plasticized polyesters or copolyesters described herein perform that function well. Biodegradable polyesters or copolyesters, while generally considered gas impermeable, nevertheless allow diffusion of odors to an extent that renders them, without some protective means, unsuitable for body waste collection pouches intended for more than extremely short durations of use. A plasticized biodegradable polyester or copolyester pouch in the condition shown in FIGS. 1 and 2 is therefore useful for periods substantially shorter than one hour as, for example, as a pouch to be used with stomal implants where the duration of use may be 30 minutes or less. Despite the odor permeability of such biodegradable polyester materials, however, pouches formed therefrom are well suited for long term body waste collection if they are used for the inner pouches of two pouch systems, as shown in FIG. 3, with odor impermeability then provided by the protective outer pouches. Any of a variety of well-known heat-sealable pouch materials that are odor impermeable are suitable for fabrication of outer pouch 10' which is not intended to be toilet flushable.

As described above, cover layer 24 of inner pouch 10 is of a porous material that is supportive when dry but has low wet strength. It should also be soft and flexible. Tissue paper that has a high percentage (preferably 100%) of cellulosic fibers is preferred such as, for example, a cellulosic tissue paper of the type available from Shawano Specialty Papers having a basis weight of 14 lb/ream. Absence of a binder is desirable because a binder may interfere with or retard the rate of disintegration, but a limited amount of a binder that is non-thermoplastic and readily soluble or disintegratable in water, such as starch, may be acceptable. The porous tissue layer for each wall 11 and 12, when such layer is in a dry state, provides reinforcement, softness, and noise reduction for the thin thermoplastic film of the inner pouch and is believed to contribute to the flushability of the film when the inner pouch is separated from the outer pouch and discarded into a flush toilet.

As believed evident from the above, the method of making a pouch-in-pouch waste collection appliance embodying this invention involves the steps of selecting a thermoplastic material for the film of the inner pouch that has a melting temperature substantially lower than that of the thermoplastic material for the film of the outer pouch and then joining together peripheral portions of the walls of the two pouches by simultaneously applying pressure and heat so that the film material of the inner pouch melts and invades the pores of the fibrous cover layer to a greater extent than the film material of the outer pouch. At the same time, the opposing or inwardly-facing film layers of the inner pouch become fused to each other, forming a true heat seal or weld between the walls of the inner pouch. Upon the subsequent application of peeling forces, the walls of the outer pouch may then be peeled away from those of the inner pouch without causing separation of the porous cover layer and film layer of the inner pouch and without disrupting the integrity of the inner pouch. The exposed inner pouch and its contents are then discarded into a flush toilet.

It will be noted from FIG. 3 that the proximal wall of the outer pouch may be similarly joined to the porous cover layer of the proximal wall of the inner pouch around the stoma-receiving opening so that as the proximal wall of the outer pouch is peeled away from the proximal wall of the inner pouch, that is, when the inner pouch is extracted from what remains of the cavity of the outer pouch, a clean separation will occur with the porous cover layer again being retained as part of the flushable inner pouch.

Other features and advantages of the invention will become apparent from the following examples:

EXAMPLE 1

Two methods are particularly suitable for the production of the tissue/film laminate of pouch 10: (1) extrusion coating onto tissue paper (1 step), and (2) film extrusion followed by lamination of the film to tissue paper (2 steps). Extrusion coating may be accomplished using a Davis Standard extrusion coating line. Tissue paper is used as a substrate and the biodegradable polyester is directly extruded onto the tissue in a single step process. With a two-step process, film may be first extruded using a blown film extrusion line and then laminated to paper tissue paper using a Faustel laminator. Lamination is ideally accomplished thermally with no adhesive layer between tissue and film. Both processes (1) and (2) give high quality laminates with no wrinkles or other defects. A two-step process is preferred because it affords better control of the adhesion and interpenetration between tissue and film. A temperature in the 165° to 220° F. range and a nip pressure in the 40–50 psi range are typically used for lamination. It is from such a laminate that the walls of the pouch may then be die-cut.

EXAMPLE 2

Blends of polycaprolactone ("Tone 787" from Dow Chemical) and triethylcitrate ("Citroflex 2" from Morflex Corp.) were compounded and pelletized using a twin-screw compounder extruder. The compounded pellets were converted into film using a cast film line equipped with a 1.25 inch extruder having an L/D ratio of 24:1. Film was extruded at a die temperature of 320° F. The following table illustrates the effect of plasticizer content on tensile modulus and noise at a film thickness of 0.6 mil (15.2 microns):

| Effect of Triethylcitrate Content (TEC) on Tensile Modulus and Noise of Polycaprolactone (PCL) | | | |
|---|---|---|---|
| | PCL Unplasticized | PCL, 10% TEC | PCL, 20% TEC |
| Tensile modulus, psi(*) | 48200 | 25600 | 9950 |
| Noise(**) | | | |
| dBA | 69 | 65 | 55 |
| dB, 8 kHz | 56 | 51 | 41 |

(*)Secant modulus at 2% elongation, ASTM D882 (initial strain rate: 10 in/in min)
(**)Film sample is formed into a cylinder and mounted on a test fixture wherein one end is held fixed and the other is rotated around the cylinder axis (15 degree angle, 70 cycles/min). Noise emissions from film flexing are analyzed with a sound level meter. dBA is a weighted average which takes into account the human perception of noise over the entire frequency range, dB in the 8 kHz octave band is indicative of the noise in the high frequency range andrepresents the crispness of the noise.

The data in this table shows that increasing triethylcitrate plasticizer content reduces the modulus of the polycaprolactone film (i.e., increases its flexibility) and reduces the noise of the film. At 20% TEC, however, film blocking, (where the surfaces of adjacent films stick together) becomes a problem. A plasticizer level of 10% is preferred because it provides adequate flexibility and quietness without blocking.

EXAMPLE 3

As ostomy pouch suitable for use as the inner pouch of a two-pouch appliance was constructed with a thin, plasticized polycaprolactone film of 0.2 to 0.6 mil (5.1 to 15.2 microns) prepared in accordance with Example 2. The pouch was found to flush well even with a low-volume toilet system (1.6 gal).

EXAMPLE 4

Another biodegradable film suitable for fabricating flushable ostomy pouches was formed by heat-lamination of a plasticized biodegradable synthetic polyester film having a thickness within the range of 0.4 to 0.8 mil (10.2 to 20.3 microns) identified as "KF02B" from Petroplast Vinora, Switzerland to a 100% cellulosic tissue having a basis weight of 14 lb/ream (product code no. 3040 from Shawano Specialty Papers).

EXAMPLE 5

The improved biodegradability of a polyester film blended with a biodegradable plasticizer is illustrated by this example.

Biodegradability was tested on film samples consisting of (1) polycaprolactone ("Tone 787" PCL from Dow Chemical) plasticized with triethylcitrate (PCL/TEC weight ratio of 90/10), (2) unplasticized PCL ("Tone 787" from Dow Chemical) and (3) a control sample of polyvinylalcohol film taken from a commercially available flushable inner pouch product ("Impact" flushable ostomy bag from Welland Medical Limited, Crawley, England). The films were exposed to aerobic sewage sludge inoculum in accordance with ASTM test method D-5209. The average weight losses were (1) 64.0%, for the plasticized PCL, (2) 26.1% for the unplasticized PCL, and (3) 12.4% for the control sample.

The plasticized PCL therefore exhibited higher weight loss due to biodegradation than the unplasticized PCL and much higher loss than the commercial PVOH inner pouch material claimed by the manufacturer to be biodegradable.

EXAMPLE 6

This example illustrates the conditions required to laminate a tissue paper to a thin biodegradable film without causing pinhole formation in the process.

A biodegradable film from Petroplast Vinora (KF02B, 20 microns thick) and a cellulosic tissue from Shawano Specialty Papers (Product Code 3040, basis weight 14 lb/ream) were heat laminated using a Faustel laminator. The nip pressure was 50 psi, the temperature 220 degrees F., and the line speed 35 to 40 feet per minute. The laminate exhibited a 180 degree peel strength in the 3–6 g/in range.

The laminate was tested for pinholes as follows: A sample of the laminate was laid on a flat surface with the film side facing up. A blue dye solution was applied on the surface of the film. After 5 minutes the film was turned over and the tissue side inspected. If pinholes were present, the dye solution would have wicked into the tissue producing visible blue dots. The test showed no evidence of pinholes. As the laminator line speed was decreased or the nip pressure increased, the peel strength became progressively higher with evidence of residual fibers embedded in the film and pinholes appeared in the dye wicking test.

EXAMPLE 7

This example illustrates the resistance to deformation imparted by tissue lamination to a thin biodegradable film.

The load at 1% and 2% strain was measured in accordance with ASTM D882-02 for the film-tissue laminate of Example 6 and for the film of Example 6 without tissue. Results are illustrated in the following table:

|  | Load @ 1% strain, MD (*) lb/in | Load @ 2% strain, MD (*) lb/in | Load @ 1% strain, TD () lb/in | Load @ 2% strain, TD () lb/in |
| --- | --- | --- | --- | --- |
| Laminate of Example 6 | 0.84 | 1.48 | 0.83 | 1.35 |
| Film of Example 6 (no tissue) | 0.35 | 0.62 | 0.54 | 0.90 |

(*) MD: machine direction
(**) TD: transverse direction

EXAMPLE 8

This example illustrates differences in heat sealing properties of films suitable for use in pouch-in-pouch appliances embodying the invention. Materials suitable for the walls of the inner pouch are heat-sealable biodegradable films of 20 microns thickness of plasticized polyester from Petroplast Vinora (KBF02B). A thermoplastic material suitable for the walls of the outer pouch is a commercial multilayer barrier film for ostomy pouches having a heat-sealable skin layer of EVA. In each test, two layers of the same film material were heat sealed together, or sought to be heat sealed together, for an interval of 1.2 seconds with a sealing element maintained at different selected temperatures and at a sealing pressure of 4 bar. Following cooling the strength of the seal (if any) was tested by manually peeling apart, or attempting to peel apart, the two layers. The results of such tests are given below:

|  | Sealing Behavior/Observation | |
| --- | --- | --- |
| Temperature | 75 Micron Commercial Barrier Film with EVA Skin Layer | 20 Micron KF02B |
| 80° C. | — | No Bonding |
| 90° C. | — | Peel |
| 100° C. | — | Peel |
| 110° C. | — | Peel |
| 120° C. | No Bonding | Peel |
| 130° C. | No Bonding | Peel |
| 135° C. | Peel | Full Seal |
| 140° C. | Peel | — |
| 150° C. | Peel | — |
| 160° C. | Peel | — |
| 170° C. | Full Seal | — |

The term "Peel" as used in the chart means that the two layers had limited adherence to each other but could nevertheless be separated or peeled apart with each layer remaining intact. "Full Seal" means that the layers had become welded or fused together and could not be so separated. The chart reveals that the KF02B film had significantly lower heat sealing temperatures than the control film. This is consistent with the DSC melting temperatures discussed earlier.

While in the foregoing I have disclosed embodiments of the invention in considerable detail for purposes of illustration, it will be understood by those skilled in the art that many of such details may be varied without departing from the spirit and scope of the invention.

I claim:

1. A biodegradable body waste collection pouch particularly suitable for flush toilet disposability; said pouch having a pair of side walls secured together along their peripheral edges to define a waste-receiving chamber therebetween; one of said side walls having a waste-receiving opening therethrough communicating with said chamber; and external attachment means provided about said opening for attachment of said pouch to a wearer; said walls of said pouch being cut from a laminate composed of (a) a layer of thin heat-sealable film impermeable to liquid and solid body wastes and of a composition comprising a biodegradable aliphatic polyester, or a biodegradable aliphatic-aromatic copolyester, or blends thereof, plasticized by one or more biodegradable plasticizers and (b) a water-disintegratable biodegradable cover layer of water-dispersible fibers having one of its surfaces uninterruptedly bonded thereto; said film having a thickness no greater than about 40 microns; said layers of said laminate being weakly bonded together and separable from each other with each layer remaining intact by the application of 180-degree peeling forces in the range of about 2 to 10 g/in.

2. The pouch of claim 1 in which said layers are separable from each other by the application of 180-degree peeling forces in the range of about 3 to 6 g/in.

3. The pouch of claims 1 or 2 in which said plasticizer is selected from the group consisting of triethylcitrate, vegetable oil, and starch, and combinations thereof.

4. The pouch of claims 1 or 2 in which said composition comprises a blend of about 70% to 95% by weight of said biodegradable aliphatic polyester or aliphatic-aromatic copolyester and about 5% to 30% by weight of said biodegradable plasticizer or plasticizers.

5. The pouch of claim 4 in which said composition comprises a blend of about 75% to 93% by weight of said biodegradable aliphatic polyester or aliphatic-aromatic copolyester and about 7% to 25% by weight of one or more of said biodegradable plasticizer or plasticizers.

6. The pouch of claim 5 in which said composition comprises a blend of about 90% by weight of said biodegradable aliphatic polyester or aliphatic-aromatic copolyester and about 10% by weight of said biodegradable plasticizer or plasticizers.

7. The pouch of claims 1 or 2 in which said aliphatic polyester or the aliphatic component of said copolyester comprises a polymer formed by ring-opening polymerization of a lactone.

8. The pouch of claims 1 or 2 in which said aliphatic-aromatic copolymer comprises a condensation product of a glycol with a combination of an aliphatic diacid and an aromatic diacid, wherein the aromatic diacid is less than 20% by mole.

9. The pouch of claims 1 or 2 in which said film has a thickness within the range of about 10 to 35 microns.

10. The pouch of claim 9 in which said film has a thickness within the range of about 15 to 30 microns.

11. The pouch of claim 9 in which said film has a sound level no greater than about 51 dB in the 8 kHz octave band when said film is formed into a cylinder and mounted on a test fixture wherein one end is held fixed and the other end is rotated about the cylinder axis at 70 cycles/min and at 15° angles.

12. The pouch of claim 9 in which said film has a secant modulus of less than about 45000 psi at 2% elongation when tested in accordance with ASTM D882-02.

13. The pouch of claim 9 in which said film of a biodegradable aliphatic polyester or copolyester is a monolayer.

14. The pouch of claim 1 in which said fibers of said water-disintegratable cover layer are cellulosic.

15. The pouch of claim 14 in which said cover layer comprises tissue paper formed of 100% cellulosic fibers.

16. The pouch of claim 1 in which said cover layer is heat-bonded to said film.

17. A pouch-in-pouch body waste collection appliance comprising an outer pouch formed of liquid, gas and odor impermeable heat-sealable polymeric film having proximal and distal side walls defining a chamber; a toilet-disposable inner pouch having proximal and distal side walls and being disposed in said chamber; said proximal walls of said inner and outer pouches having aligned body waste receiving openings therethrough; and attachment means for attaching said proximal walls of said inner and outer pouches in areas surrounding said openings to skin surfaces of a patient about a body waste discharge orifice; said disposable inner pouch having walls formed from sheet material composed of (a) a layer of thin heat-sealable film impermeable to body wastes of a composition comprising a biodegradable aliphatic polyester, or a biodegradable aliphatic-aromatic copolyester, or blends thereof, plasticized by one or more biodegradable plasticizers and (b) a water-disintegratable, porous, biodegradable cover layer of water-dispersible fibers bonded thereto; said heat-sealable film of said inner pouch having a melting temperature lower than that of the heat-sealable film of said outer pouch; said walls of said outer and inner pouches having peripheral edge portions heat-sealed together with the peripheral edge portions of said cover layer being bonded more securely to the film material of said inner pouch than to the film material of said outer pouch.

18. The body waste collection appliance of claim 17 in which said film of said outer pouch has a melting temperature at least 10 degrees C. higher than the melting temperature of said heat-sealable inner pouch film.

19. The body waste collection appliance of claims 17 or 18 in which said composition comprises a blend of about 70% to 95% by weight of said biodegradable aliphatic polyester or aliphatic-aromatic copolyester and about 5% to 30% by weight of said biodegradable plasticizer.

20. The body waste collection appliance of claim 19 in which said composition comprises a blend of about 75% to 93% by weight of said biodegradable aliphatic polyester or aliphatic-aromatic copolyester and about 7% to 25% by weight of said biodegradable plasticizer.

21. The body waste collection appliance of claim 20 in which said composition comprises a blend of about 90% by weight of said biodegradable aliphatic polyester or aliphatic-aromatic copolyester and about 10% by weight of said biodegradable plasticizer.

22. The body waste collection appliance of claims 17 or 18 in which said aliphatic polyester or the aliphatic component of said copolyester comprises a polymer formed by ring-opening polymerization of a lactone.

23. The body waste collection appliance of claims 17 or 18 in which said aliphatic-aromatic copolymer comprises a condensation product of a glycol with a combination of an aliphatic diacid and an aromatic diacid, wherein the aromatic diacid is less than 20% by mole.

24. The body waste collection appliance of claims 17 or 18 in which said film of said inner pouch has a thickness no greater than about 40 microns.

25. The body waste collection appliance of claim 24 in which said film has a thickness within the range of about 10 to 35 microns.

26. The body waste collection appliance of claim 25 in which said film has a thickness within the range of about 15 to 30 microns.

27. The body waste collection appliance of claims 17 or 18 in which said fibers of said water disintegratable cover layer are cellulosic.

28. The body waste collection appliance of claim 27 in which said cellulosic fiber cover layer comprises tissue paper.

29. The body waste collection appliance of claim 28 in which said tissue paper is 100% cellulosic fibers.

30. A pouch-in-pouch body waste collection appliance comprising an outer pouch formed of liquid, gas and odor impermeable heat-sealable polymeric film having proximal and distal side walls defining a chamber; a toilet-disposable inner pouch having proximal and distal side walls and being disposed in said chamber; said proximal walls of said inner and outer pouches having aligned body waste receiving openings therethrough; and attachment means for attaching said proximal walls of said inner and outer pouches in areas surrounding said openings to skin surfaces of a wearer about a body waste discharge orifice; said disposable inner pouch having walls formed of (a) a layer of a heat-sealable film impermeable to body wastes having a thickness no greater than about 40 microns and of a composition comprising a biodegradable aliphatic polyester, or a biodegradable aliphatic-aromatic copolyester, or blends thereof, plasticized by one or more biodegradable plasticizers and (b) a water-disintegratable, porous, biodegradable cover layer of water-dispersible fibers having substantially an entire surface of said cover layer, except for its peripheral edges, weakly bonded to said inner pouch film; said weak bond permitting separation of said surface of said cover layer from said inner pouch film, with both remaining substantially intact, by the application of 180 degree peeling forces in the range of about 2 to 10 g/in.

31. The appliance of claim 30 in which said weak bond permits separation of said surface of said cover layer from said inner pouch film, with both remaining substantially intact, by the application of 180 degree peeling forces in the range of about 3 to 6 g/in.

32. The appliance of claims 30 or 31 in which said composition comprises a blend of about 70% to 95% by weight of said biodegradable aliphatic polyester or aliphatic-aromatic copolyester and about 5% to 30% by weight of said biodegradable plasticizer.

33. The appliance of claim 32 in which said composition comprises a blend of about 75% to 93% by weight of said biodegradable aliphatic polyester or aliphatic-aromatic copolyester and about 7% to 25% by weight of said biodegradable plasticizer.

34. The appliance of claim 32 in which said composition comprises a blend of about 90% by weight of said biodegradable aliphatic polyester or aliphatic-aromatic copolyester and about 10% by weight of said biodegradable plasticizer.

35. The appliance of claims 30 or 31 in which said aliphatic polyester or the aliphatic component of said copolyester comprises a polymer formed by ring-opening polymerization of a lactone.

36. The appliance of claims 30 or 31 in which said aliphatic-aromatic copolymer comprises a condensation product of a glycol with a combination of an aliphatic diacid and an aromatic diacid, wherein the aromatic diacid is less than 20% by mole.

37. The appliance of claims 30 or 31 in which said film of said inner pouch has a thickness within the range of about 10 to 35 microns.

38. The appliance of claim 37 in which said film of said inner pouch has a thickness within the range of about 15 to 30 microns.

39. The appliance of claims 30 or 31 in which said fibers of said cover layer are cellulosic.

40. The appliance of claim 39 in which said cellulosic fiber cover layer comprises tissue paper.

* * * * *